United States Patent [19]

Derrick

[11] Patent Number: 5,046,491
[45] Date of Patent: Sep. 10, 1991

[54] APPARATUS AND METHOD FOR RESPIRED GAS COLLECTION AND ANALYSIS

[76] Inventor: Steven J. Derrick, 1077 Huston Dr., West Mifflin, Pa. 15122

[21] Appl. No.: 611,429
[22] Filed: Oct. 17, 1990

Related U.S. Application Data

[63] Continuation of Ser. No. 499,977, Mar. 27, 1990, abandoned.

[51] Int. Cl.$^5$ .................. A61M 15/08; A61B 5/08
[52] U.S. Cl. .................. 128/200.24; 128/204.18; 128/207.18; 128/716; 128/730; 128/719; 128/911
[58] Field of Search .................. 128/203.12, 203.22, 128/204.11, 204.18, 207.18, 200.24, 730, 716, 718, 719, 725, 911, 912

[56] References Cited

U.S. PATENT DOCUMENTS

D. 262,322 12/1981 Mizerak .................. D29/7
4,263,908 4/1981 Mizerak .................. 128/205.25
4,699,139 10/1987 Marshall et al. .................. 128/207.18
4,915,104 4/1990 Marcy .................. 128/207.18

OTHER PUBLICATIONS

Bio Chem International Catalog; "A Complete Line of Disposable & Accessories for $CO_2$ & Apnea Monitoring".

Primary Examiner—Edgar S. Burr
Assistant Examiner—Eric P. Raciti
Attorney, Agent, or Firm—Lawrence G. Zurawsky; Thomas F. Shanahan

[57] ABSTRACT

Apparatus and method for selective, separate or simultaneous collection and analysis of nasal gases and oral gases, and mixtures thereof, respired by a patient, with optional simultaneous delivery to the patient of selected inhalant gases. The apparatus comprises a nasal gas cannula and an oral gas capture member constructed and arranged to avoid or minimize contact with the patient's mouth and other facial surfaces.

18 Claims, 2 Drawing Sheets

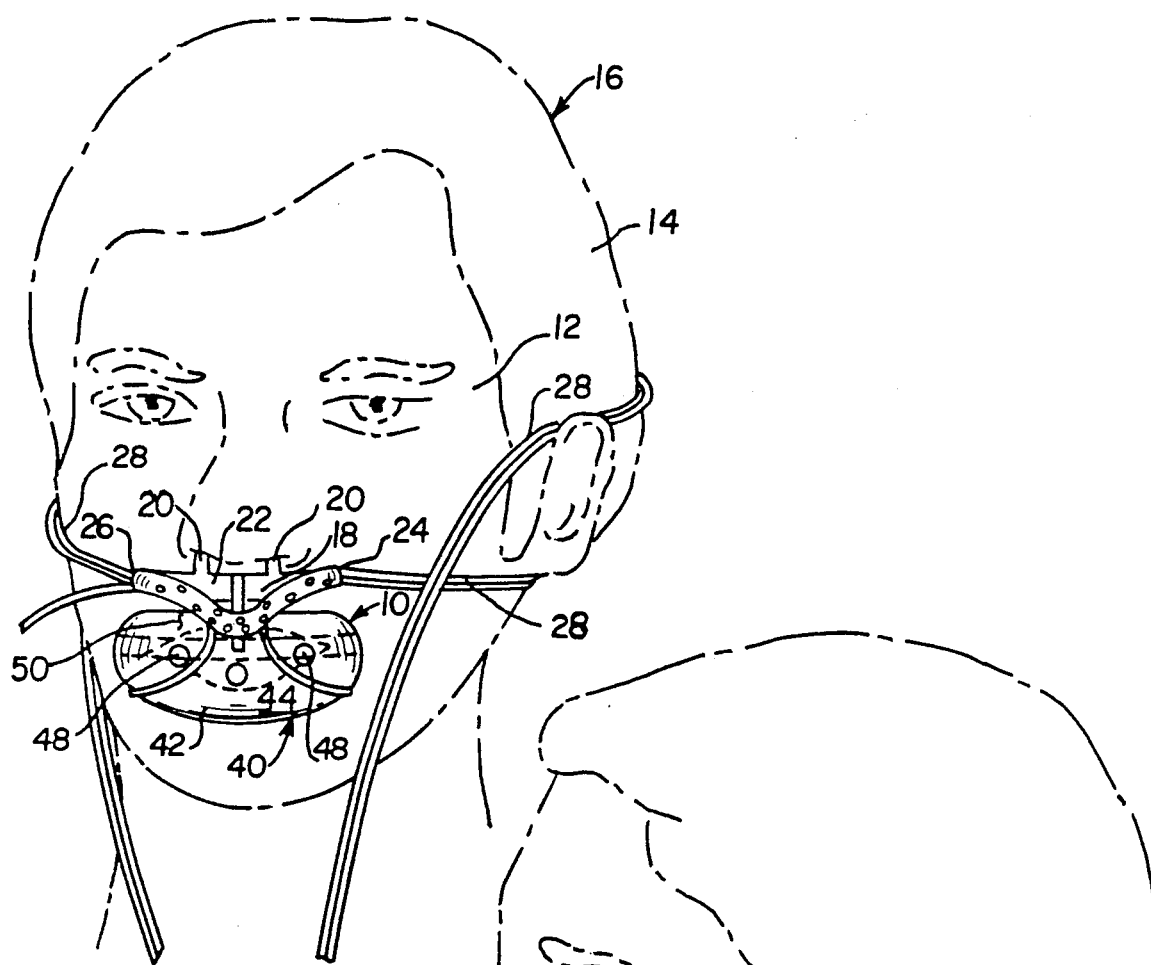
FIG_1
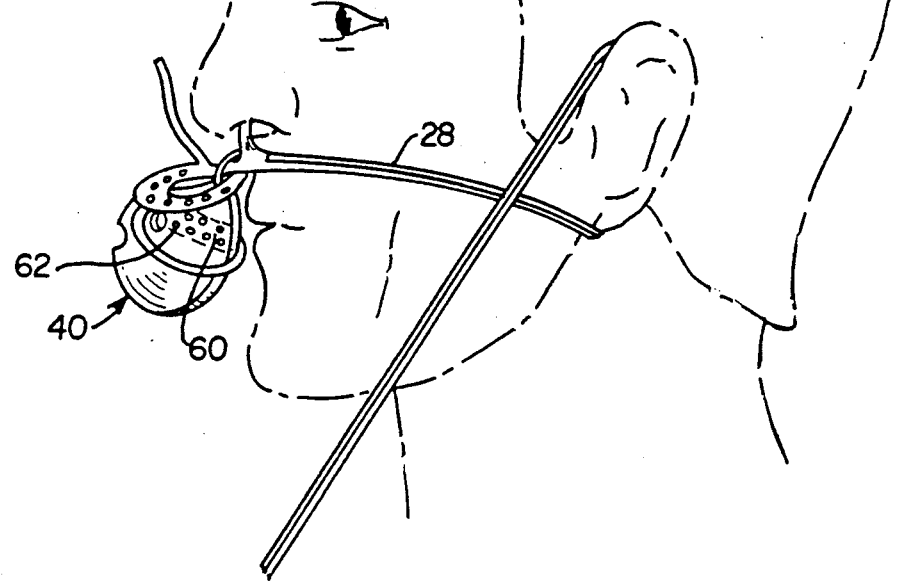
FIG_2

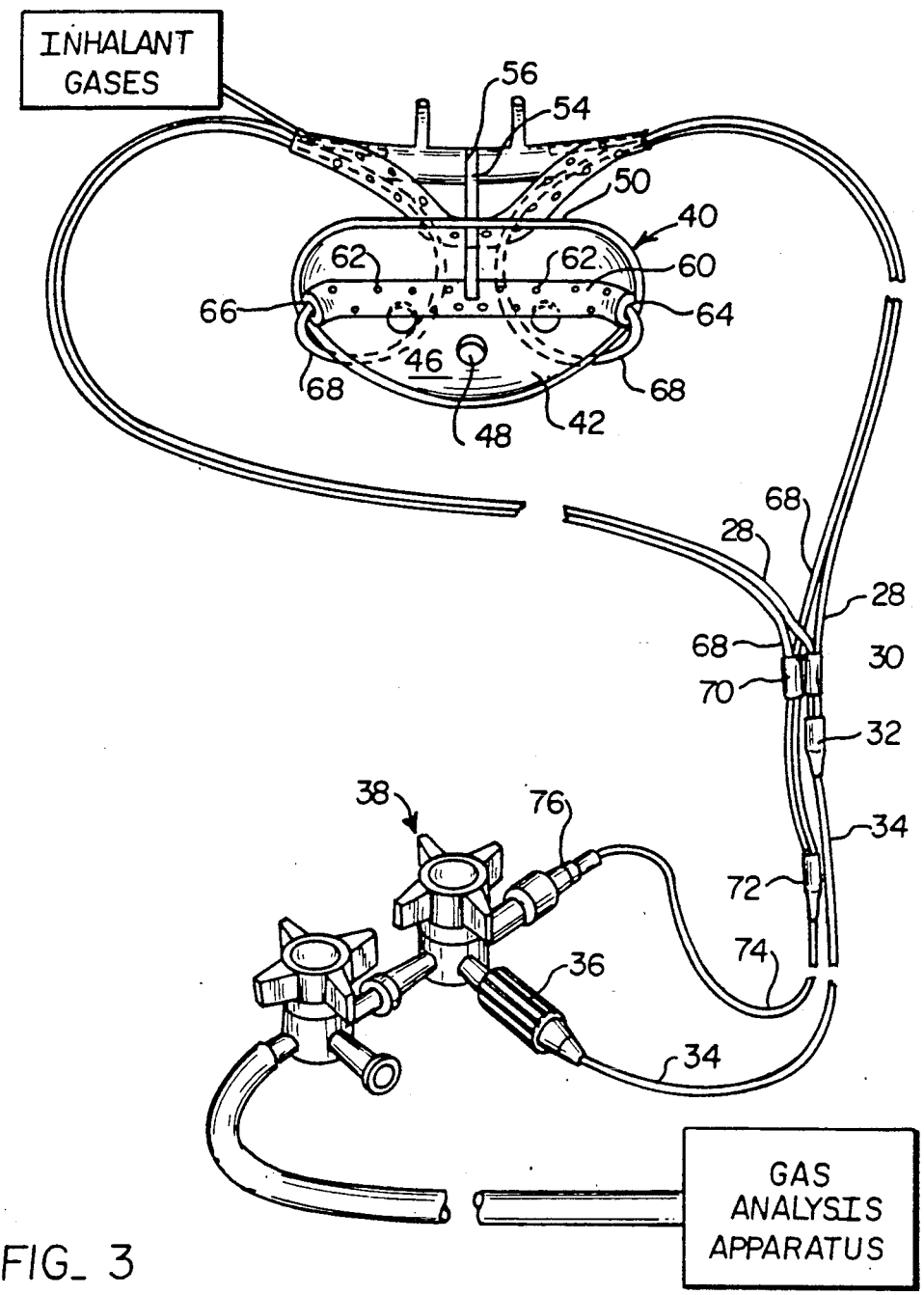
FIG_ 3
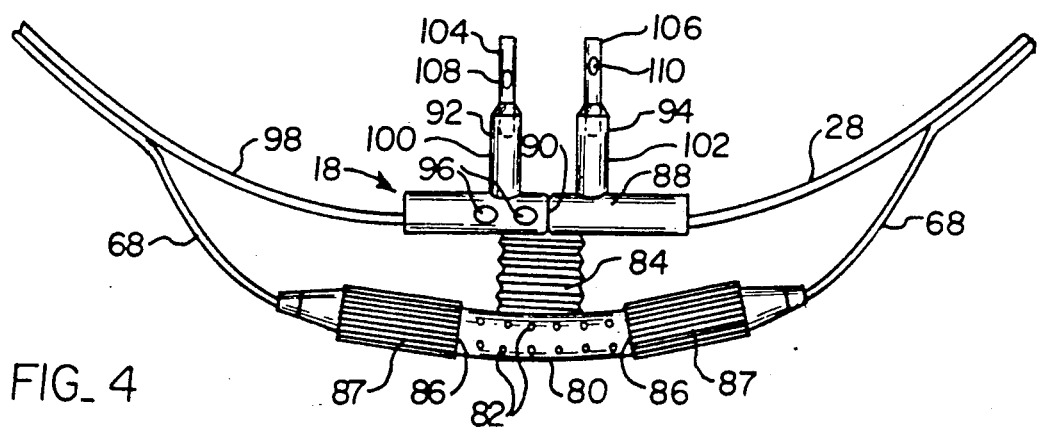
FIG_ 4

APPARATUS AND METHOD FOR RESPIRED GAS COLLECTION AND ANALYSIS

This is a continuation of copending application Ser. No. 07/499,977 filed on Mar. 27, 1990, now abandoned.

BACKGROUND OF THE INVENTION

1. Field of the Invention

This invention relates to apparatus and methods for collection and analysis of gases respired by a patient and further for capnometric analysis of those gases for content of carbon dioxide and other gases.

2. Description of the Prior Art

During anesthesia, and especially during sedation anesthesia or analgesic anesthesia, it is often desirable to collect and analyze qualitatively and quantitatively the constituents of gases respired by the patient. During such procedures, it is further desirable to avoid or minimize the use of gas delivery and collection apparatus that is so large or complicated that it interferes with anesthesia procedures or surgical procedures or interferes with a clear, unobstructed view of the patient's face and respiration passages. Furthermore, it is desirable during such procedures to avoid or minimize contact between the gas delivery and collection apparatus and the patient's mouth and other facial areas, especially to assure optimum comfort of the patient and freedom from claustrophobic reaction in the patient. The prior art discloses several types of apparatus and methods intended to alleviate those problems and achieve those objectives.

U.S. Pat. No. 4,248,218 to Fischer discloses a scavenging mask apparatus for administering gas to a patient and scavenging the gas while preventing its leaking to the ambient atmosphere. That patent describes use of nasal cannulas for delivery of gas and emphasizes maintaining a substantially fluid tight seal between the mask and surfaces of the patient's face. There is no disclosure in that patent of means for simultaneous or alternate, separate, selective collection and analysis of exhaled or inhaled nasal gases and exhaled or inhaled oral gases.

U.S. Pat. No. 4,265,239 to Fischer, Jr., et al. discloses another type of apparatus to limit or prevent escape of anesthetic gases into the ambient atomosphere of a dental orperatory. Leaking gases are drawn by vacuum into a gas exhaust chamber formed between adjacent, separated mask walls. That patent teaches maintenance of fluid tight contact between the edges of the mask and the facial surfaces of the patient and does not describe any method for selective, simultaneous or alternate, separate, selective, collection and analysis of gases respired via the patient's nose and mouth.

U.S. Pat. No. 4,763,664 to Merilainen discloses apparatus for collecting exhaled gases to determine carbon dioxide content and respiratory quotient, which apparatus consists of a closed, transparent canopy or container surrounding the patient's head and sealed around the patient's neck. That patent does not describe any apparatus or method for selective, separate or combined, simultaneous collection of orally and/or nasally respired gases.

U.S. Pat. No. 4,807,617 to Nesti discloses a double mask type apparatus with a fluid tight seal between the delivery mask and the facial surfaces of the patient and an evacuated exhaust chamber between the delivery mask and the exhaust mask to capture gases leaking around the edges of the delivery mask. That apparatus can be used only with standard, prior art delivery mask apparatus. That patent contains no description of an apparatus or method for selective, separate or simultaneous collection and analysis of orally and/or nasally respired gases.

A number of prior art patents disclose apparatus for delivery of inhalation gases to the atmosphere near the patient's nose and mouth while maintaining the gas delivery apparatus out of contact with the patient's facial surfaces. For example, U.S. Pat. No. 3,877,691 to Foster discloses a pair of concave shield panels which are joined around their peripheral edges to form between them an exhaust chamber for gases exhaled by the patient which flow into the shield apparatus through apertures in the arcuate panel proximal to the patient's face. Attached to the interior surface of the perforated arcuate panel is a delivery tube for oxygen. U.S. Pat. No. 3,403,677 to Struve discloses a facial surgical drape support including a perforated tubular loop for introduction of oxygen or air into the space between the supported drape and the patient's face. U.S. Pat. No. 4,739,753 to Brehm discloses a surgical drape support including a delta-shaped gas supply nozzle, spaced above the patient's face and having apertures directing to the patient's breathing area a supply of air, oxygen or anesthetic gases. U.S. Pat. No. 3,530,515 to Jacoby describes a surgical drape support including a rigid frame member supporting a flexible oxygen tube which is spaced from, and directed toward, the patient's breathing passages. U.S. Pat. No. 2,628,803 to Krewson discloses a surgical drape support which has mounted above the patient's face a rigid, slotted plate or cup to be used in administering anesthetics to the patient. None of those patents describes any method or apparatus for the selective, separate simultaneous or alternate collection and discriminating analysis of orally and/or nasally respired gases.

Other prior art patents disclose additional types of apparatus adapted to collect and/or analyze exhaled gases. For example, U.S. Pat. No. 4,848,366 to Aita, et al, describes a mask covering the users nose, mouth, chin and cheeks and forming a substantially fluid tight chamber around those facial areas for containing exhaled gases which are exhausted from that chamber by a self-contained exhaust fan system carried on the user's body. That patent does not describe any method or apparatus for selective, discriminating collection and removal, separately or simultanously, of respired nasal gases and respired oral gases.

U.S. Pat. No. 3,395,701 to Bartlett, et al, discloses apparatus for collecting, isolating and analyzing expired gases to measure the oxygen content therein. That apparatus can be used only with standard, prior art oxygen breathing masks and makes no provision for selective, separate or simultaneous discriminating collection and analysis of respired nasal and oral gases.

Apparatus manufactured by Nellcor Incorporated of Hayward, California for delivery of inhalant oxygen gas and collection of expired carbon dioxide includes an apparatus body mounted under the patient's nose and a pair of separate cannulas, each extending into a separate nare of the patient. One cannula delivers oxygen to the patient and the other cannula collects exhaled carbon dioxide. That apparatus does not provide for the selective, separate, simultaneous or alternative collection and discriminating analysis of respired oral and/or nasal gases.

There remains a need for a method, and for simply constructed, light weight apparatus, for selective, discriminating separate and/or simultaneous collection and analysis of respired nasal and/or oral respired gases which can be used while avoiding substantial contact with the facial surfaces of the patient.

SUMMARY OF THE INVENTION

In accordance with the present invention, there are provided a method and apparatus for selective and discriminating, separate or simultaneous collection and anaylsis of respired nasal gases and respired oral gases from a patient. In a preferred embodiment of the invention, method and means are provided for delivery of inhalant gases to the patient's respiratory passages, simultaneous with respired gas collection and analysis. In the apparatus of this invention, there are provided nasal respired gas cannula means and oral respired gas capture means, each separately connected to distribution means, all constructed and arranged for selective, discriminating collection and distribution for analysis of either a separate nasal respired gas sample, or a separate oral respired gas sample, or a mixture of nasal and oral respired gases.

Accordingly, it is an object of the present invention to provide a method and apparatus for selective, discriminating collection and analysis of separate oral and nasal respired gases, or combinations thereof.

It is another object of this invention to provide simple, light weight apparatus for simultaneous separate or combined collection of respired nasal and/or oral gases, which apparatus, in use, avoids or minimizes contact between the apparatus and the patient's facial surfaces.

It is a further object of this invention to provide apparatus which enables separate, discriminating collection and analysis of nasal respired gases compared to oral respired gases.

It is yet another object of this invention to provide simple, light weight apparatus that enables continuous and discriminating monitoring of the patient's breathing patterns comprising nasal respiration, oral respiration, and combinations thereof.

Those and other objects of the present invention will be more completely disclosed and described in the following specification, the accompanying drawings and the appended claims.

BRIEF DESCRIPTION OF THE DRAWINGS

FIG. 1 depicts part of the respired gas collection apparatus and the inhalant gas delivery apparatus of the present invention mounted on the face of a patient.

FIG. 2 depicts portions of the respired gas collection apparatus and the inhalant gas delivery apparatus mounted on a patient's face and substantially spaced from contact with the facial surfaces of the patient.

FIG. 3 depicts the apparatus of this invention connected in fluid communication with collected, distribution means, collected gas analysis means and inhalant gas reservoir means.

FIG. 4 depicts a preferred embodiment of the apparatus of this invention having a single, light weight tubular oral gas collection member of relatively small dimension and a nasal cannula member comprising inhalant gas delivery means with respired gas collection means.

DESCRIPTION OF THE PREFERRED EMBODIMENTS

To facilitate understanding of the nature, scope and preferred aspects of this invention, the terms set forth below, as used herein, shall have the meanings and connotations indicated.

The term "respired gases" includes both inhaled gases and exhaled gases.

The term "patient" includes any living subject, human or otherwise, whether being subjected to anesthesia, surgery, medical treatment, examination, diagnosis, experimentation or any other procedure involving respiration of gases.

The term "gas" includes all gases, vapors, and mixtures and solutions of gases and/or vapors.

The term "end tidal" refers to the latter, last or final portion of a volume of gas exhaled by a patient.

The terms "expired" and "expiration" refer to gases exhaled, and the act of exhaling, by a patient.

The terms "inspired" and "inspiration" refer to gases inhaled, and the act of inhaling, by a patient.

The term "capnometry" refers to analysis and measurement of a gas for carbon dioxide content and percentage composition. The term "capnograph" refers to a chart, table or other pictorial or visual representation of gas analysis data setting forth carbon dioxide content and percentage composition.

The term "J.E.T. NasOrCap" is a trademark adopted by the inventor of the subject invention to identify the source of the "Joyce End Tidal NasOrCap" apparatus of this invention, and all of its various embodiments and designs.

The term "J.E.T. NasOrCap" also refers to a service mark adopted by the inventor to identify the source of the method of the subject invention described herein.

For purposes of brevity and clarity hereinbelow, the term "nasal gas" will be used to refer to nasal respired gases, the term "oral gas" refers to oral respired gases, and the term "gas" refers to respired gas, unless specifically and explicitly indicated otherwise in the context of the use of those terms in any particular instance below.

The phrase "inhalant gas" refers to a gas such as oxygen, or air, or a mixture of oxygen and air or of oxygen and water vapor, or other mixture of gases; or to anesthetic gases such as nitrous oxide or other volatile anesthetics, or any mixture or combination of any of them, as long as such inhalant gas is administered or delivered to a patient for inhalation during any procedure.

DESCRIPTION OF THE PREFERRED EMBODIMENTS

The method of this invention includes collecting and transporting separately or simultaneously those gases respired via a patient's nose and those gases respired via a patient's mouth during any surgical, anesthetic, diagnostic, experimental or other procedure. Nasal respired gases and oral respired gases are collected intermittently or simultaneously whether the patient alternates between nasal and oral respiration, or whether the patient simultaneously respires both orally and nasally. The collected and captured nasal and/or oral respired gases are conducted separately to a distribution and valve assembly constructed and arranged to permit discharge from its effluent port of either nasal gas separately, or oral gas separately, or a mixture of nasal and oral gases.

Respired gases are analyzed by any selected, preferred technique including infrared spectrometry, mass spectrometry, or any other desired or suitable analytic technique or procedure. In a preferred embodiment, such analysis is performed on site in the operating, examining or treating theater, with results being converted by analog means to a graph or other analog reproduction of the analytic data, and/or with conversion of such data through proper interfacing apparatus into digital read-out data.

The method and apparatus of this invention permit constant, unobstructed monitoring and observation by the anesthetist of a patient's obstructed or unobstructed air ways, breathing patterns, facial expressions, somatic movements and of analytic data read-out apparatus, thereby improving the efficiency, safety, and effectiveness of the anesthesia and operatory procedures and techniques. In particular, prompt effective detection of patient apnea, choking and regurgitation are enabled and enhanced by the method and apparatus of this invention.

DETAILED DESCRIPTION OF THE DRAWINGS

The nature, scope and preferred embodiments of the method and apparatus of this invention can be understood better by reference to the accompanying drawings. In FIG. 1, the respired gas collection and transport apparatus of this invention is referred to generally by reference numeral 10 and is shown mounted on the face 12 and head 14 of a patient indicated generally by reference numeral 16. Collection and transport apparatus 10 include a nasal respired gas cannula member 18, from which there extend a pair of cannulas 20 extending into the nares of the patient's nose. The length of a cannula extending into the interior of the nare is determined by considerations of patient comfort and effectiveness of collection of nasal gas. Experience with various prototypes of the apparatus of this invention indicates that an accurate, representative, substantially undiluted and uncontaminated sample of nasal gas is obtained with the apparatus of this invention because undiluted and uncontained quantities of nasal exhaled gas are held within the sinuses and driven toward the cannulas for collection and capture with force of exhalation, excluding possibly diluting or contaminating gases and materials. As shown in the drawings, cannula body member 18 supports two cannulas 20, 20 used for nasal gas collection. As is explained more fully hereinbelow, it is within the concept of this invention that, in appropriate circumstances, collection of nasal gas can be accomplished using only a single cannula for that purpose. Alternatively with a pair of cannulas, one may be used for inhalant gas delivery, while the other is used for respired gas collection or sampling.

Cannula member 18 includes a hollow body portion 22 having at least one of its end portions 24 and 26 open to permit fluid communication with a nasal exhaled gas conduit 28. It is within the concept of this invention that only one end 24 or 26 of cannula hollow body member 22 be open to fluid communication with nasal gas conduit 28. In another embodiment of this invention as shown in the drawings, both ends 24 and 26 of cannula hollow body member 22 are open and in fluid communication with a pair of nasal exhaled gas conduits 28 and 28. In that embodiment of this invention, as depicted more clearly in FIG. 3, the two nasal gas conduits 28 and 28 are, at some point distal from the patient, collect together within a nasal conduit collar 30 and eventually are mutually connected to a nasal conduit manifold 32, from the opposite end of which a single nasal gas sample conduit 34 extends to a valve connector 36 which connects nasal sample conduit 34 to sample gas distribution and valve means, indicated generally by reference No. 38 in FIG. 3.

Oral respired gas capture apparatus is referred to generally by reference numeral 40 in FIG. 1, and includes an oral respired gas hood 42, having an outwardly convex surface shown as 44 in FIG. 1 and a concave surface shown as 46 in FIG. 3 facing inwardly toward the patient's face 12.

Oral gas hood 42 of oral gas capture means 40 has formed therein a plurality of chimneys 48, constructed and arranged to permit flow of air or other gases through chimneys 48 when apparatus 10 is in use. Although a plurality of chimneys 48 is shown in the drawings, it is within the concept of this invention that oral gas hood 40 contain a single chimney 48 in those preferred embodiments for which a single chimney 48 is more suitable or efficient.

Chimneys 48 permit flow of ambient air into the space between oral gas hood 42 and the patient's mouth to facilitate more effective breathing by the patient during inhalation. In addition, chimneys 48 improve exhaust flow of nasal gases from the area surrounding the patient's mouth during those respiration cycles when the patient is breathing nasally. An upper portion 50 of the outer, convex surface 44 of oral gas hood 42 is connected by bonding material, a suitable fastener, or other suitable connecting means (not shown in the drawings) to a flexible, adjustable, connecting stem 54, which is attached at its other end 56 to an outer surface of nasal cannula hollow body member 22. In other embodiments within the concept of this invention, connecting stem 54 can be fastened to the inner, concave surface 46 of oral gas hood 42. In addition, other suitable means can be used to connect oral gas body member 42 to nasal cannula hollow body member 22, or to any other portion of the gas collection and transport apparatus 10, as long as the connecting means substituted for connecting stem 54 is adjustable to enable the purpose and object of this invention in providing oral and nasal gas collecting and capture apparatus that is sufficiently close to the patient's nares and mouth to permit optimally effective gas collection and sampling, while avoiding or minimizing contact between the gas collection apparatus and the patient's facial surfaces. Those purposes and objects are substantially effected by the apparatus as depicted most clearly in FIG. 2, in which there is no contact between the oral gas capture assembly 40 and the patient's face 12, and in which there is no, or little contact, between nasal gas cannulas 20 and the patient's nose or nares. Avoidance, or minimization, of contact between the gas collection and transport apparatus 10 and the patient's facial surfaces 12 are desirable and necessary to facilitate anesthesia, surgery, other treatment and patient monitoring and to avoid claustrophobic and other undesirable reactions in the patient.

Capture of orally respired gases is achieved by a hollow bodied oral gas capture member 60, which can be constructed of tubing, having formed in its walls a plurality of apertures 62 to permit flow of oral gases into capture member 60. In certain preferred embodiments of this invention, oral gas capture member 60 has a single aperture 62 oriented substantially with the center of the patient's oral cavity to assure that only oral respired gas is captured, with no, or a minimal amount of, ambient atmosphere or nasal gas mixed with the oral gas. Another circumstance that tends to exclude ambient atmosphere or other ambient gases, including nasal gas, from captured oral end tidal gas is the outwardly directed forces exerted by oral exhalation of gas, which forces and convention currents tend to drive ambient gases and nasal gas away from apertures 62 in oral gas capture body member 60 during the oral exhalation process. Either one or both of ends 64 and 66 of oral gas capture member 60 are connected in fluid communication with the connecting end of tubular oral gas conduit 68, a pair of which are shown in FIG. 3. Similar to the arrangement of nasal gas conduits 28, at some point distal from the patient, the pair of oral gas conduits 68, 68 are collected in an oral gas conduit collar 70, through which the pair of conduits 68, 68 extend for ultimate mutual connection to one end of an oral gas conduit manifold 72, from the other end of which there extends an oral gas sample conduit 74, which is connected at its other end by connecting means 76 to sample gas distribution and valve means 38.

As shown in FIGS. 1, 2 and 3, oral gas hood 42 has an approximate ellipsoidal peripheral configuration with a major axis and a minor axis, each somewhat larger than the length and height, respectively, of the patient's mouth. Although such configuration and dimensions are suitable with various preferred embodiments of the apparatus of this invention, other embodiments of the apparatus have proved suitable for particular purposes. For example, minimization of patient discomfort and minimization of interference with medical processes and procedures have been achieved by changing the peripheral configuration of oral gas hood 42 and by reducing its major and minor axes to lengths substantially less than the length and height, respectively, of the patient's mouth, and by positioning that particular oral gas hood in substantial alignment with the multidimensional point of symmetry of the oral cavity and as close thereto as possible, while avoiding or minimizing contact with the patient's mouth or face and avoiding interference with comfortable respiration.

In another preferred embodiment of this invention, as shown in FIG. 4, the oral gas capture means comprises a hollow flexible oral gas capture cylinder 80, connected to nasal gas cannula member 18 by connecting stem 84 and located near the patient's facial surfaces between the patient's upper lip and nares. As shown in FIG. 4, the oral gas capture means comprises a single capture cylinder 80; however, in other preferred embodiments, a plurality of capture cylinders 80 can be used. Capture cylinder 80 has a plurality of oral gas ports 82 to conduct oral gases into the interior of capture cylinder 80. Oral gas ports 82, 82 can be of any shape and configuration suitable for a particular preferred embodiment of this invention.

As depicted further in FIG. 4, connecting stem 84 consists of a corrugated connecting member, thereby imparting more strength and flexibility to facilitates ease of placement and relative location between nasal gas cannula body member 18 and oral gas capture cylinder 80. The end portions 86 and 86 of oral gas capture cylinder 80 are connected by suitable connectors 87, 87 to fluid communication means such as oral gas conduits 68 and 68, to oral gas collar 70, oral gas conduit manifold 72, and oral gas sample conduit 74 to connecting means 76 and sample gas distributed and valve means 38.

In a preferred embodiment of the apparatus of this invention having a single oral gas capture cylinder 80, said cylinder is constructed of a flexible, plastic tube having an inside diameter of approximately 0.25 inch and a length of approximately 1.0 inch.

Another preferred embodiment of the apparatus of this invention is explained with reference to FIG. 4. The nasal gas cannula body member 88 has a solid central portion 90 which prevents fluid communication between nasal cannulas 92 and 94. One of those cannulas, such as cannula 92, is used for delivery of inhalant gas to the patient while the other cannula 94, is used simultaneously for collection of respired nasal gas for sampling and analysis. The portion of cannula body member 88 located below the base of cannula 92 contains one or more inhalant gas ports 96 for delivery of oxygen and other inhalant gases to the region between the patient's nose and mouth. The oxygen and other inhalant gases are conducted to cannula body member 88 through inhalant gas conduit 98 which communicates with inhalant gas storage and delivery means, not shown in FIG. 4.

Cannulas 92 and 94, as depicted in FIG. 4, each have a base member, 100 and 102 respectively, connected at their lower portions to body member 88 of nasal gas capture means 18. In addition, each of cannulas 92 and 94 have an upper tubular member, 104 and 106 respectively, which is slideably mounted in the cannula base member, 92 and 94 respectively, to provide slideable, telescopic mounting of the upper cannula members in the cannula base members. That construction enables adjusting each of the cannulas shown in FIG. 4 to accommodate the particular needs of a particular patient. In addition, to their top end openings, each of cannulas 92 and 94 have formed therein one or more gas ports 108 and 110. Those gas ports 108 and 110 are incorporated in those preferred embodiments of this invention in which they are useful to maximize or optimize gas flow through the cannulas.

The various embodiments of the apparatus of this invention depicted in FIG. 4 and discussed with relation to FIG. 4 are preferred because such embodiments limit patient discomfort, are simply constructed and light weight, and cause minimal obstruction of the patient's facial surfaces and breathing passages. In addition, such preferred embodiments provide effective collection of respired gases, especially expired oral gases, which tend to travel upwardly over the patient's upper lip toward the patient's nose.

As shown and described herein, the preferred materials of construction used with the apparatus of this invention are light weight, flexible plastic tubing, sheeting and other stock materials. Nevertheless, it is within the concept of the method and apparatus of this invention that the elements of structure of the apparatus of this invention can be constructed from any material that is not harmful to, or causes discomfort to, the patient and that does not affect adversely the gas delivery, collection, sampling and analysis functions of the apparatus and method of this invention.

As is shown in FIG. 1, 2 and 3, contact with the patient's head and facial surfaces is minimized by the method of mounting and supporting the apparatus of this invention on the patient. The oral gas capture assembly is maintained out of contact with the patient's facial services while the nasal gas cannula member is in limited contact with the upper lip of the patient. The expired gas conduits 28 and 68 can be passed below the patient's ears and around the patient's head and back around the tops of the patient's ears, where they pass down across the patient's chest and are joined in collars 30 and 70 (FIGS. 1 and 3). Alternatively, the expired gas conduits can be looped over each ear of the patient and passed downwardly over the patient's chest to be joined in collars 30 and 70 (FIGS. 2 and 3). Other methods of supporting the apparatus of this invention on the facial surfaces of the patient are within the concept of this invention as long as minimization of patient contact, discomfort and claustrophobic reaction are balanced with the objective of optimizing respired gas collection and transport.

The method and apparatus of this invention have been tested on at least 25 patients using various embodiments of the apparatus of this invention. That patient testing indicates that, during respiration involved in the medical procedures described herein, a majority or substantial portion of the expired gases flow over the patient's upper lip toward the patient's nostrils. Such patient testing also indicates that, of the 25 patients tested, approximately 40 per cent of the patients exhibited oral respiration most of the time, and more than 60 per cent of the patients tested exhibited substantial periods of simultaneous nasal and oral respiration or frequent intermittent periods of nasal respiration alternating with oral respiration. The apparatus of this invention provides the advantage and substantial improvement of enabling more effective capture and analysis of expired oral gases and nasal gases. In addition, the apparatus of this invention provides substantial improvement and advantage in the ability to measure the fraction of total oxygen inspired from the total atmospheric gases. Another improvement and advantage provided by the apparatus of this invention was demonstrated during testing of the apparatus with patients, which testing demonstrated an improved ability by the attendant anesthetist to observe and monitor continuously and closely changes in patient breathing patterns and behavior, with a consequent improved ability to detect and remedy obstructions of the patient's respiratory passages.

According to the provisions of the patent statutes, I have explained the principles, preferred constructions, and modes of operation of my invention and have illustrated and described what I now consider to represent its best embodiments. However, it should be understood that, within the scope of the appended claims, the invention may be practiced otherwise then as specifically illustrated and described.

Therefore, I claim:

1. Apparatus for collecting, transporting, sampling and analyzing nasal and oral gases respired by a patient, said apparatus comprising
   cannula means constructed and arranged for placement in at least one of the patient's nares,
   said cannula means having at least one opening distal from the patient's nare for conducting respired nasal gases,
   a nasal respired gas conduit having at least two spaced openings, with one of said openings connected in fluid communication with the respired gas opening of the cannula means and the other end of said nasal respired gas conduit connected to respired gas distribution means,
   oral respired gas capture means for placement near the patient's mouth,
   said oral respired gas capture means comprising a hollow member having at least one aperture therein to permit aggregation of oral respired gases therein and having at least one effluent opening for the removal of oral respired gases therefrom, and
   an oral respired gas conduit independent from said nasal respired gas conduit, having at least two spaced openings therein, with one of said openings connected in fluid communication with the effluent opening of said oral respired gas capture means and the other end of said oral respired gas conduit connected to said respired gas distribution means.

2. Apparatus for collecting, transporting, sampling and analyzing gases respired by a patient, said apparatus comprising
   cannula means constructed and arranged for placement in at least one of the patient's nares,
   said cannula means having at least one opening distal from the patient's nare for conducting respired nasal gases, and
   a nasal respired gas conduit having at least two spaced openings, with one of said openings connected in fluid communication with the respired gas opening of the cannula means and the other end of said nasal respired gas conduit connected to respired gas distribution means, and
   oral respired gas capture means suspended from said cannula means near the patient's mouth, and
   said oral respired gas capture means having a hollow member having at least one aperture therein, constructed and arranged to permit aggregation of oral respired gases therein and having at least one effluent opening for the removal of oral respired gases therefrom, and
   an oral respired gas conduit having at least two spaced openings therein, with one of said openings connected in fluid communication with the effluent port of said oral respired gas capture means and the other end of said oral respired gas conduit connected to said respired gas distribution means.

3. Apparatus as described in claim 2 and including
   inhalant gas delivery means mounted on said apparatus near the patient's nose and mouth and having at least one end of said delivery means open for fluid communication, and
   an inhalant gas conduit having at least two spaced openings therein, with one of said openings connected in fluid communication with the opening in the inhalant gas delivery means and the other end of said inhalant gas conduit connected in fluid communication with a source of gases to be delivered to the patient for inhalation by the patient, and
   said inhalant gas delivery means having at least one aperture therein constructed and arranged to deliver into the ambient atmosphere around the patient's nose and mouth said gas delivered for inhalation by the patient.

4. Apparatus as described in claim 2 wherein said nasal respired gas conduit and said oral respired gas conduit are each separately connected to valve means constructed and arranged for selective delivery from said valve means of a sample gas comprising gas selected from a class including said nasal respired gas separately, and said oral respired gas separately, and a mixture of said oral respired gas and said nasal respired gas.

5. Apparatus as set forth in claim 2 wherein said nasal respired gas conduit and said oral respired gas conduit are connected in fluid communication with analytical means adapted for analysis and determination of the concentrations of carbon dioxide and other gases respired by the patient.

6. Apparatus as described in claim 3 wherein said inhalant gas delivery means comprises a gas delivery tube having formed therein at least one aperture constructed and arranged to permit diffusion of said respired gas into the ambient atmosphere surrounding the patient's nose and mouth.

7. Apparatus as described in claim 6 wherein said gas delivery tube comprises a portion of said cannula means.

8. Apparatus as described in claim 2 wherein said oral respired gas capture means comprises
a hood member near the patient's mouth, and
an oral gas capture tube, having formed therein at least one aperture constructed and arranged for passage of oral respired gas through said aperture into said oral gas capture tube.

9. Apparatus as described in claim 2, wherein said oral respired gas capture means comprises a hood member having formed therein at least one aperture permitting flow of ambient gases through said hood member.

10. Apparatus as described in claim 2, wherein said oral respired gas capture means is connected to said nasal respired gas cannula means by an adjustable connecting member constructed and arranged to facilitate positioning said oral respired gas capture means near, but spaced from, the patient's mouth and other facial surfaces when the cannula means is inserted in the nare of the patient.

11. Apparatus as described in claim 2 wherein said cannula means comprise
a cannula body member, and
a cannula base portion connected to said cannula body member, and
a cannula tube slidably mounted in said cannula base member for adjustment of the length of said cannula tube inserted into the patient's nose.

12. Apparatus as described in claim 2 wherein
said cannula means comprise first and second separate cannulas, and
said first cannula is connected to inhalant gas delivery means, and
said second cannula is connected to said nasal respired gas conduit.

13. A method for selective collection and analysis of gas respired by a patient comprising
collecting nasal respired gas in the patient's nare, and
collecting oral respired gas, and
separately conducting each of said oral respired gas and said nasal respired gas to a distribution zone, and
conducting from said distribution zone a sample gas comprising one or more gases selected from a class of gases including said nasal respired gas, and said oral respired gas, and a mixture of said nasal respired gas and said oral respired gas, and
analyzing said sample gas for the presence and concentrations of preselected constituents.

14. A method as described in claim 13 wherein said nasal respired gas and said oral respired gas are simultaneously and separately collected.

15. A method as described in claim 13 including
introducing, into the ambient atmosphere near the patient's nose and mouth, a preselected inhalation gas.

16. A method as described in claim 13 including
introducing, into the ambient atmosphere near the patient's nose and mouth, an inhalation gas comprising a mixture of oxygen and water vapor.

17. A method as described in claim 13 including
introducing, into the ambient atmosphere near the patient's nose and mouth, an inhalation gas comprising a mixture of oxygen and analgesic gases.

18. A method as set forth in claim 13 including
introducing, into the ambient atmosphere surrounding the patient's nose and mouth, an inhalant gas comprising a mixture of oxygen and anesthetic gases.

* * * * *